United States Patent [19]
Wachsman et al.

[11] Patent Number: 5,985,476
[45] Date of Patent: *Nov. 16, 1999

[54] STABLE HIGH CONDUCTIVITY FUNCTIONALLY GRADIENT COMPOSITIONALLY LAYERED SOLID STATE ELECTROLYTES AND MEMBRANES

[75] Inventors: Eric D. Wachsman, Palo Alto; Palitha Jayaweera, Fremont; David M. Lowe, Hayward; Bruce G. Pound, Menlo Park, all of Calif.

[73] Assignee: Gas Research Institute, Chicago, Ill.

[*] Notice: This patent is subject to a terminal disclaimer.

[21] Appl. No.: 08/678,344

[22] Filed: Jul. 11, 1996

Related U.S. Application Data

[62] Division of application No. 08/428,629, Apr. 25, 1995, Pat. No. 5,725,965.

[51] Int. Cl.$^6$ .............................. H01M 8/12; C23F 13/00
[52] U.S. Cl. .............................. 429/33; 429/304; 204/296
[58] Field of Search ............................ 429/304, 33, 30, 429/191; 204/296

[56] References Cited

U.S. PATENT DOCUMENTS

| | | |
|---|---|---|
| 3,956,194 | 5/1976 | Armand . |
| 4,242,426 | 12/1980 | Arendt . |
| 4,683,181 | 7/1987 | Armand et al. . |
| 4,793,904 | 12/1988 | Mazanec et al. . |
| 4,802,958 | 2/1989 | Mazanec et al. . |
| 4,812,329 | 3/1989 | Isenberg . |
| 4,931,214 | 6/1990 | Worrell et al. . |
| 4,933,054 | 6/1990 | Mazanec et al. . |
| 4,952,330 | 8/1990 | Leger et al. . |
| 5,001,021 | 3/1991 | Maricle et al. . |
| 5,006,494 | 4/1991 | Virkar . |
| 5,045,170 | 9/1991 | Bullock et al. . |
| 5,069,987 | 12/1991 | Gordon . |
| 5,171,645 | 12/1992 | Khandkar . |
| 5,183,801 | 2/1993 | Virkar et al. . |
| 5,213,911 | 5/1993 | Bloom et al. . |
| 5,240,480 | 8/1993 | Thorogood et al. . |
| 5,273,628 | 12/1993 | Liu et al. . |
| 5,298,235 | 3/1994 | Worrell et al. . |
| 5,306,411 | 4/1994 | Mazanec et al. . |
| 5,350,641 | 9/1994 | Mogensen et al. ...................... 429/30 |
| 5,364,506 | 11/1994 | Gür et al. . |

OTHER PUBLICATIONS

E. D. Wachsman, N. Jiang, D. M. Mason, and D. A. Stevenson, Proceedings of the First International Symposium on Solid Oxide Fuel Cells, Electrochem. Soc., 89–11, 15 (1989) . (No month).
C. Wang, X. Xu, and B. Li, Solid State Ionics, 13, 135 (1984). (No month).
P. Duran, J. R. Jurado, C. Moure, N. Valverde, and B. C. H. Steele, Mat. Chem. Phys., 18, 287 (1987). (No month).
R. N. Blumenthal, F. S. Brugner, and J. E. Garnier, J. Electrochem. Soc., 120, 1230 (1973). (No month).
I. Riess, J. Electrochem. Soc., 128, 2077–2081 (1981). (No month).
I. Riess, Solid State Ionics, 52, 183 (1992). (No month).
P. Han, R. Mukundan, P. K. Davies, and W. L. Worrell, Mixed–Conducting; Oxides in Solid Oxide Fuel Cells, EPRI/GRI Fuel Cell Workshop on Fuel Cell Technology Research and Development, Mar. 22–23, 1994, Atlanta, Georgia.
E. D. Wachsman, G. R. Ball, N. Jiang, and D. A. Stevenson, Solid State Ionics, 52, 213 (1992). (No month).
I. Riess, Solid State Ionics, 52, 127, (1992). (No month).
H. Yahiro, Y. Baba, K. Eguchi, and H. Arai, Electrochem. Soc., 135, 2077 (1988). (No month).
A. C. Khandkar and A.V. Virkar, GRI Annual Technical Report 5086–294–1292, Gas Research Institute, Chicago (1988). (No month).
D. Choi, G. Tong, and A. Sanjurjo, SRI IR&D Report (Feb. 1990).
"Aging Phenomenon of Stabilized Bismuth Oxides," Materials Research Bulletin, vol. 29, No. 3, pp. 247–254 (1994). (No month).

*Primary Examiner*—John S. Maples
*Attorney, Agent, or Firm*—Pauley Petersen Kinne & Fejer

[57] ABSTRACT

Stable high conductivity functionally gradient compositionally layered solid bodies suitable for use as electrolytes and membranes and providing improved oxygen-ion conductivity for electrolytes and improved mixed oxygen-ion and electronic conductivity for membranes. The electrolytes provide solid oxide fuel cells with high efficiency operation at 300° to 800° C.

25 Claims, 8 Drawing Sheets

STABLE HIGH CONDUCTIVITY FUNCTIONALLY GRADIENT COMPOSITIONALLY LAYERED SOLID STATE ELECTROLYTES AND MEMBRANES

This is a divisional of application Ser. No. 08/428,629 filed on Apr. 25, 1995, now U.S. Pat. No. 5,725,965.

BACKGROUND OF THE INVENTION

1. Field of the Invention

This invention relates to stable high conductivity functionally gradient compositionally layered solid state electrolytes and membranes providing improved oxygen-ion conductivity for electrolytes and improved mixed oxygen-ion and electronic conductivity for membranes. The electrolytes of this invention are useful in solid oxide fuel cells and as sensors. The membranes of this invention are useful in gas separation and in membrane reactors. Multi-layered solid electrolytes and membranes of this invention have a mixed conducting anodic portion with high oxygen ionic conduction and electronic conduction on one side, preferably of the n-type, which may be exposed to a reducing atmosphere, and interface on the opposite side with a high oxygen ionic conducting and low electronic conducting portion for the electrolyte and high p-type ionic conducting for the membrane, and exposed to an oxidizing atmosphere on the opposite side.

2. Description of Related Art

Oxygen ion conductors based upon $Bi_2O_3$ have been known for solid electrolytes and oxygen separation due to their high oxygen ion conductivity and their ability to operate at lower temperatures. There have been various attempts to improve their phase stability and their thermodynamic stability against reduction. U.S. Pat. Nos. 5,006,494 and 5,183,801 teach the phase stability of $Bi_2O_3$ in the cubic form stabilized by 10 to 40 mole percent of a rare earth oxide, such as yttria, is enhanced by inclusion of up to 10 mole percent of an oxide of a cation having a valence of 4 or greater, such as zirconia, hafnia, thoria, stannic oxide, tantalum oxide, and niobium oxide as a dopant. It has been shown that $Bi_2O_3$ stabilized in the δ-phase by 20 mol % $Er_2O_3$ has ionic conductivity in the order of 1 to 2 orders of magnitude greater than that of yttria stabilized zirconia at comparable temperatures. E. D. Wachsman, N. Jiang, D. M. Mason, and D. A. Stevenson, Proceedings of the First International Symposium on Solid Oxide Fuel Cells, Electrochem. Soc., 89–11, 15 (1989). $Bi_2O_3$ has been reported to exhibit purely ionic conduction down to low partial pressures of oxygen of $10^{-20}$ atm. E. D. Wachsman, G. R. Ball, N. Jiang, and D. A. Stevenson, Solid State Ionics, 52, 213 (1992); C. Wang, X. Xu, and B, Li, Solid State Ionics, 13, 135, (1984); and P. Duran, J. R. Jurado, C. Moure, N. Valverde, and B. C. H. Steele, Mat. Chem. Phys., 18, 287 (1987). Ionic conduction at low oxygen pressure has been observed only in the absence of a reducing agent. The reducing environments of fuels, such as methane and hydrogen, decompose $Bi_2O_3$ to metallic bismuth. Wachsman, Ball, Jiang, and Stevenson, supra.

Problems of the reducibility of $Bi_2O_3$ electrolytes has been recognized and various attempts have been made to solve the problem. U.S. Pat. No. 5,213,911 teaches a solid oxide low temperature electrolyte with very low electron conduction and stable in $H_2$ formed by combination of a compound having weak intramolecular metal-oxygen interactions with one having stronger metal-oxygen interactions.

A graded zirconia-bismuth oxide electrolyte is taught by U.S. Pat. No. 5,171,645 having a $Bi_2O_3$ doped for increased oxygen ion transport rich layer on one side and a $ZrO_2$ doped for increased oxygen ion transport rich layer on the opposite side with gradations of the components between, enabling low temperature operation and better thermal expansion stability in a solid oxide fuel cell. In another embodiment, both surfaces are doped $ZrO_2$ rich layers graded to a relatively thick doped $Bi_2O_3$ rich central layer.

Aliovalent doped ceria in the fluorite structure is also known to exhibit ionic conductivity significantly greater than yttria stabilized zirconia at comparable temperatures. R. N. Blumenthal, F. S. Brugner, and J. E. Garnier, J. Electrochem. Soc., 120, 1230 (1973). However, ceria electrolytes have a high electronic conduction in a reducing environment. U.S. Pat. No. 5,001,021 teaches limiting electronic conduction in ceria electrolytes by double metal doping.

A mixed oxygen ion and electronic conductor may favor n-type electronic conduction in a reducing environment while in an oxidizing environment it may favor p-type conduction. Thus, in theory a mixed conductor may exhibit pure ionic conduction over a central region between the n-type and p-type regions. I. Riess, J. Electrochem. Soc., 128, 2077–2081 (1981) and I. Riess, Solid State Ionics, 52, 183 (1992). The use of mixed conductors for the entire anode/electrolyte/cathode structure has been investigated, but no significant electrolytic region was detected. P. Han, R. Mukundan, O. K. Davis, and W. L. Worrell, Mixed Conducting Oxides in Solid Fuel Cells, EPRI/GRI Fuel Cell Workshop on Fuel Cell Technology Research and Development, Mar. 22–23, 1994, Atlanta, Ga. This work was an extension of single component solid oxide bodies with n-type conductance on one side and p-type conductance on the opposite side of an oxygen ion conducting central portion taught by U.S. Pat. No. 5,298,235 wherein appropriate conduction is induced by chemical modification, doping, or by chemically tailoring electronic conducting perovskites to produce an oxygen ion conducting electrolyte central portion.

Use of ionic conductors for electrocatalytic chemical reactions is known. U.S. Pat. Nos. 4,793,904; 4,933,054; and 4,802,958 teach a solid electrolyte of $Bi_2O_3$ stabilized by a lanthanide or calcium oxide having a conductive coating on one side capable of reducing oxygen to oxygen ions and a conductive coating on the opposite side capable of desired oxidative catalysis. Use of mixed ionic-electronic conductors for electrocatalytic chemical reactions is taught by U.S. Pat. No. 5,273,628 which teaches thin membranes of homogeneous solid solutions and non-homogeneous mixtures of $Bi_2O_3$ stabilized with a stabilizer, such as Y, and containing a variable valence j metal, such as Ti. U.S. Pat. No. 5,306,411 teaches multi-phase mixtures of an electronically conductive material and an oxygen ion conductive material based upon $ABO_3$ perovskites, preferably containing small amounts or no bismuth.

Problems of physical stability of solid oxygen conducting electrolytes have been recognized. U.S. Pat. No. 5,069,987 teaches a solid oxide fuel cell having an electrolyte with repeating array of ductile ordered, continuous metallic fibers imbedded in the ceramic matrix, such as expanded Ni foil.

Mixed oxygen ion and electronic conductors have been used in electrodes as taught by U.S. Pat. No. 5,364,506 which teaches a stabilized $ZrO_2$ electrolyte and mixed conducting perovskite anode; U.S. Pat. No. 4,931,214 teaches an electrode of $ZrO_2$ with an oxide stabilizing agent, such as $Y_2O_3$, and a metal oxide, such as $TiO_2$; U.S. Pat. No. 4,812,329 teaches solid oxygen conducting electrolytes with bonded anodes of particles of electronic conductor partly embedded in a skeleton of ceramic metal oxide with its surface covered with a separate, porous, gas permeable mixed oxygen ionic-electronic conducting coating; and U.S. Pat. No. 3,956,194 teaches positive electrodes of monophased graphite having an alkali cation, a transition metal, and a non-metallic electronegative atom.

U.S. Pat. No. 5,240,480 teaches an oxygen ion conducting membrane having a porous layer with average pore sizes of less than about 10 microns and a contiguous dense non-porous layer, both materials being a mixed ionic-electronic conducting multicomponent metallic oxide, such as perovskites.

SUMMARY OF THE INVENTION

Oxygen ion conducting electrolytes of this invention are suitable for a wide variety of uses, including oxygen sensors and so lid oxide fuel cells. Cells using electrolytes have conductive regions of n-type|intrinsic|p-type conduction. The intrinsic region has essentially exclusive high oxygen conductivity. To obtain the same conductivity as current state of the art fuel cells using yttrium-stabilized zirconia at a lower temperature, the material must have higher mobility of and/or a greater concentration of oxygen-ion vacancies. Ideally, to limit power dissipation by electronic conduction, this conductivity should be exclusively ionic, $t_i=\sigma_i/\sigma_t=1$, wherein $t_i$ is the transport number, $\sigma_i$ is the oxygen ion conductivity, and $\sigma_t$ is the total conductivity. Numerous oxide structures, such as fluorite, pyrochlore, perovskite, and brownmillerite, are being considered as potential intermediate temperature electrolytes, but perovskites and similar structures having high conductivities have unacceptably high electronic conductivity, such that $t_i$ is less than 0.9. Suitable for use as an essentially exclusive high oxygen ion conductor in this invention are those materials having $t_i$ greater than about 0.95, and preferably greater than 0.99. By the terminology essentially exclusive ionic conducting, as used in this description and claims, we mean having an ionic conductivity of $t_i>0.95$, and preferably $t_i>0.99$. Bismuth oxide-based materials having the above mentioned ionic conductivity are suitable in addition to $Bi_2O_3$ itself, such as bismuth-metal(s)-oxide as disclosed in U.S. Pat. No. 5,213,911, as well as rare earth-metal(s)-oxide and lanthanum-metal(s)-oxide, both as disclosed in U.S. Pat. No. 5,213,911, and multiple metal doped bismuth oxides as disclosed in U.S. Pat. Nos. 5,006,494 and 5,183,801. Any other metal oxide having $t_i>0.95$, and preferably $t_i>0.99$, is suitable.

When a reducing environment is adjacent the anodic side of the cell, the stability of the oxygen-ion conducting material may be reduced. According to this invention, the major oxygen ion conductor is protected from the reducing environment by a dense layer of mixed ionic-electronic conductor which is tolerant to the reducing environment and raises the oxygen partial pressure to greater than that providing stability at its interface with an adjacent essentially exclusive high oxygen ion conductor. Any material which provides such mixed ionic-electronic conductivity under reducing conditions and provides sufficiently high partial pressure of oxygen at the interface is suitable. We have found ceria-based materials to be suitable. oxygen ion conducting membranes according to this invention are suitable for a wide variety of uses, including oxygen separation and in membrane reaction systems for chemical conversions. Systems using membranes have conductive regions of either n-type or p-type, or preferably, n-type|p-type with no intrinsic region and providing high electronic conduction throughout. When a reducing environment is adjacent the anodic side of the system, the n-type conductor which is tolerant of the reducing environment protects the stability of the adjacent mixed oxygen ion conductor. Suitable n-type conductors are the same as those set forth above for electrolytes. Suitable mixed ionic-electronic conductors for the p-type conductor include $Bi_2O_3$ and bismuth oxide-based materials, such as mixed metal bismuth oxides as disclosed in U.S. Pat. No. 5,273,628, and perovskite materials as disclosed in U.S. Pat. No. 5,306,411 which have the required mixed ionic-electronic conduction.

This invention will be primarily described and demonstrated with respect to oxygen ion conductance in solid oxide fuel cells, but it will be recognized that the stable high conductivity functionally gradient compositionally layered solid state electrolyetes and membranes of this invention may utilize other conducting materials for other ion conduction for a variety of other uses.

Solid oxide fuel cells offer a desirable process for conversion of chemical energy directly to electricity since they produce negligible $NO_x$, and due to their high fuel efficiency, produce less $CO_2$ per kilowatt hour than most alternative processes. Current solid oxide fuel cells, based upon solid zirconia electrolytes, must operate at about 1000° C. and above to avoid unacceptably high ohmic losses. These high operating temperatures reduce selection of suitable electrode and interconnect materials and induce adverse structural changes in the cell as well as constraints on fabrication, thus increasing costs. Yttria-stabilized zirconia has been used as the electrolyte in solid oxide fuel cells due to its most favorable compromise in chemical and thermal stability, ionic conductivity, and cost, but the limitations imposed by its high operating temperatures render a low commercial feasibility of such cells.

Thin film, on the order of about 5 microns, yttria-stabilized zirconia electrolytes which would reduce the operating temperature required to obtain ohmic losses comparable to current thick film electrolytes, about 100 microns, have been considered. However, thin films of an electrolyte with a higher ionic conductance would further reduce the temperature requirement or increase te cell power density at the same temperature.

In addition, zirconia based solid oxide fuel cells still require high fabrication temperatures, in the order of about 1200° to 1700° C., which sinters attached electrodes resulting in lower specific surface area, decreased electrocatalytic activity, and higher electrode polarization losses, making an intermediate temperature electrolyte of a more advantageous material highly desirable.

It is an object of this invention to provide electrolytes and membranes having high ionic conductance which are stable with a reducing environment on one side and an oxidizing environment on the opposite side.

Another object of this invention is to provide electrolytes and membranes having high oxygen ion conductance at temperatures lower than 800° C., and down to about 300° to about 500° C.

Yet another object of this invention is to provide low cost, intermediate temperature, solid oxide fuel cells using a multi-layered electrolyte having a dense mixed ionic and electronic conducting ceria-based layer and a dense oxygen-ion conducting bismuth oxide based layer providing increased open circuit potential, increased power density, and greater electrolyte stability than fuel cells using prior ceria-based or bismuth oxide-based electrolytes.

It is another object of this invention to provide an electrolyte for solid oxide fuel cells which operates at intermediate temperatures of less than about 800° C., allowing use of a wider range of materials for electrode and interconnect components of the cell.

Another object of this invention is to provide a multi-layered ceria-based|bismuth oxide-based oxygen ion conducting electrolyte, or membrane, which can be fabricated without the requirement of high processing temperatures during fabrication, reducing problems of warpage, delamination, interdiffusion, and thermal mismatch.

The superior ionic conductors based upon bismuth oxide and ceria have not been used as electrolytes in reducing environments, such as in solid oxide fuel cells, because they are readily reduced in the presence of reducing fuel gases at the anode. Bismuth oxide electrolytes have the advantage, in addition to a lower operating temperature, that their required processing temperatures during fabrication is about 850° C., only about half that required by yttrium-stabilized zirconia, resulting in a much wider selection of compatible materials and ease of fabrication. While the lower limit of stability of bismuth oxide is subject to some controversy involving a kinetically limited decomposition to metallic Bi, $Bi_2O_3$-based electrolytes have been found to exhibit purely ionic conduction down to $10^{-20}$ atm $P_{O_2}$, but only in the absence of an active reducing agent. Ceria, by contrast, is not reduced to metallic cerium, but $Ce^{+4}$ is reduced to $Ce^{+3}$, resulting in mixed ionic and electronic conduction with decreasing $P_{O_2}$. The usefulness of ceria as an electrolyte is limited by $t_i$ being less than 1.0 with decreasing $P_{O_2}$ resulting in lower open-circuit potential and power loss by electronic conduction.

This invention involves use of stable high conductivity functionally gradient compositionally layered solid state electrolytes, which, in the case of oxygen ion conductance, result in the synergistic combination of the superior ionic conductors $Bi_2O_3$ and $CeO_2$ as the electrolyte in an intermediate temperature solid oxide fuel cell. A dense, mixed ionic/electronic conducting metal oxide layer facing the reducing atmosphere acts as a protective layer for a high oxygen ion conducting electrolyte layer and, in principle, can serve as the anode itself. By the terminology dense, as used throughout this description and in the claims, we mean non-porous with no through connecting porisity. Use of such a mixed ionic/electronic conducting layer means that the electrode can be non-porous since the electron transfer reaction does not require the presence of a three-phase boundary between the electrode, electrolyte, and reactant, as is necessary when the electrode is purely an electronic conductor. The mixed conducting metal oxide layer also allows charge transfer to occur over the entire electrode surface due to the mobility of both electrons and oxygen ions. A dense mixed conducting layer, therefore, protects the stabilized $Bi_2O_3$ from the reducing environment and avoids materials problems associated with maintaining a porous structure for gas diffusion to the electrolyte-electrode interface, allowing good utilization of bismuth oxide's high oxygen ion conductivity in a solid oxide fuel cell. The bismuth oxide also blocks electronic conductance through the ceria-based mixed ionic/electronic conducting layer due to increase its desired higher ionic conductance.

The relative electronic conductivity contribution of a mixed oxygen ion/electron conductor depends upon the local oxygen activity. Under a reducing environment, electron conductivity may exceed ionic conductivity, forming an n-type conductor, and in an oxidizing environment, electronic conductivity may exceed ionic conductivity, forming a p-type conductor. The relative electronic contribution to conductivity decreases with distance from the active gas interface. As a result of the mixed ionic and electronic conducting properties and their dependence upon local oxygen activity, a dense layer of a mixed conductor can act as an anode and also protect an adjacent layer of high oxygen ion conductor, such as $Bi_2O_3$, from reduction by a reducing atmosphere, such as fuel in a fuel cell. The oxygen pressure gradient across these layers is fixed by the oxygen partial pressure of the gas phase on either side with the gradient within each layer being a function of the thickness of the layer. Thus, in a bi-layered mixed ionic-electronic conductor|ionic conductor structure, the local oxygen activity at the interface of the layers may be increased to the concentration where the oxygen ion conducting portion is stable by increasing the thickness of the mixed ionic-electronic conductor, relative to that of the ionic conductor. FIG. 1 schematically illustrates the effect of the relative thicknesses of the mixed ionic-electronic conducting anodic electrolyte layer and the ionic conducting electrolyte layer upon the partial pressure of oxygen at their interface. The interface of the mixed ionic-electronic conducting anodic electrolyte layer and the ionic conducting electrolyte layer is $X_{E/A}$. The left hand portion illustrates a relatively thin anodic electrolyte layer with a thicker ionic conducting electrolyte layer, while the right hand portion illustrates a relatively thick anodic electrolyte layer with a thin ionic conducting electrolyte layer. As illustrated, the oxygen partial pressure at the exposed face of the anodic-electrolyte layer is $P_{O_2}^0$ while the oxygen partial pressure at the exposed face of the ionic conducting electrolyte layer is a higher value $P_{O_2}^L$. The $P_{O_2}$ gradient across the entire electrolyte is shown as linear for simplicity. It is seen that the partial pressure of oxygen at the mixed conductor anodic electrolyte|oxygen ion conductor electrolyte interface $P_{O_2}^{E/A}(2)$, obtained with the relatively thick mixed conducting anodic electrolyte layer, is much higher than $P_{O_2}^{E/A}(_1)$ obtained with the relatively thin mixed conducting anodic electrolyte layer. This illustrates the functionally gradient aspect of the electrolytes of this invention by controlling the partial gas pressure at the interface of the compositionally layered materials.

In the case of $Bi_2O_3$, the $Bi_2O_3$ electrolyte layer is stable at partial pressures of oxygen greater than about $10^{-20}$-$10^{-13}$ atm. Since electronic conduction in $Bi_2O_3$ electrolytes is minimal, $t_i=1.0$, full theoretical open-circuit voltage is obtainable with a thin $Bi_2O_3$ layer adjacent a thicker mixed ionic-electronic conducting layer. The mixed ionic-electronic conducting layer should have both comparable ionic conductivity, so that an increase in relative thickness of a mixed conducting anode has minimal effect on resistance, and a structure similar to the thin ionic conducting layer to reduce interfacial stresses due to lattice mismatch as well as mismatch due to different thermal expansion characteristics. $CeO_2$ stabilized in the fluorite type structure fills both of these requirements. Thus, a $CeO_2$ layer can act as both an anode, n-type, and electrolyte, depending upon the local oxygen partial pressure.

In an intermediate temperature solid oxide fuel cell, the electrolyte can be considered as a bi-layered structure of $Bi_2O_3$ and $CeO_2$, with the $CeO_2$ layer exposed to the fuel environment. This structure provides an intermediate temperature solid oxide fuel cell having many benefits in terms of materials compatibility, selection and fabrication, avoiding processing and fabrication limitations associated with current high temperature electrolytes which have limited development and commercialization of solid oxide fuel cells.

The bi-layered electrolyte structure, based upon highly conductive $CeO_2$ and $Bi_2O_3$ according to this invention, exhibits the synergistic effect of a higher open circuit potential than either material separately as a single layered electrolyte. Further, the bi-layered electrolyte structure using these materials according to this invention exhibits high stability against reduction by hydrogen at the anode of a fuel cell.

One preferred bi-layered electrolyte structure according to this invention, especially suitable for intermediate temperature solid oxide fuel cells, is the bi-layered structure of $MO_x—CeO_2|M'O_y—Bi_2O_3$ wherein M and M' are single metals or mixtures of metals including: Ca, Sr, Ba, Y, Zr, Nb, Mo, Hf, W, La, Ce, Pr, Nd, Pm, Sm, Eu, Gd, Tb, Dy, Ho, Er, Tm, Yb, and Lu. The dopant metal and its concentration is chosen on the basis of resulting ionic and electronic conductivities, the compatibility of these conductivities at the oxygen partial pressures of the anode-gas and anode-electrolyte interfaces, phase stability, and a matching of thermal coefficients of expansion between the two layers. The bi-layered structures are preferred to be as thin as possible consistent with fabrication methods and physical stability. For example, bi-layered electrolytes are generally thin films, about 1 to about 30 microns, of $M'_xO_3-Bi_2O_3$ on relatively thick, about 10 $\mu m$ to about 1.0 mm thick layer of $M_yO_3-CeO_2$. The mixed ionic-electronic conducting electrolyte layer should be sufficiently thick to provide sufficiently high oxygen partial pressure at its interface with the oxygen ion conducting electrolyte layer to provide high stability against chemical reduction.

BRIEF DESCRIPTION OF THE DRAWINGS

Achievement of the above objects and further advantages of this invention are more completely described with respect to preferred embodiments and reference to the drawings, wherein.

DESCRIPTION OF PREFERRED EMBODIMENTS

Figure 1:
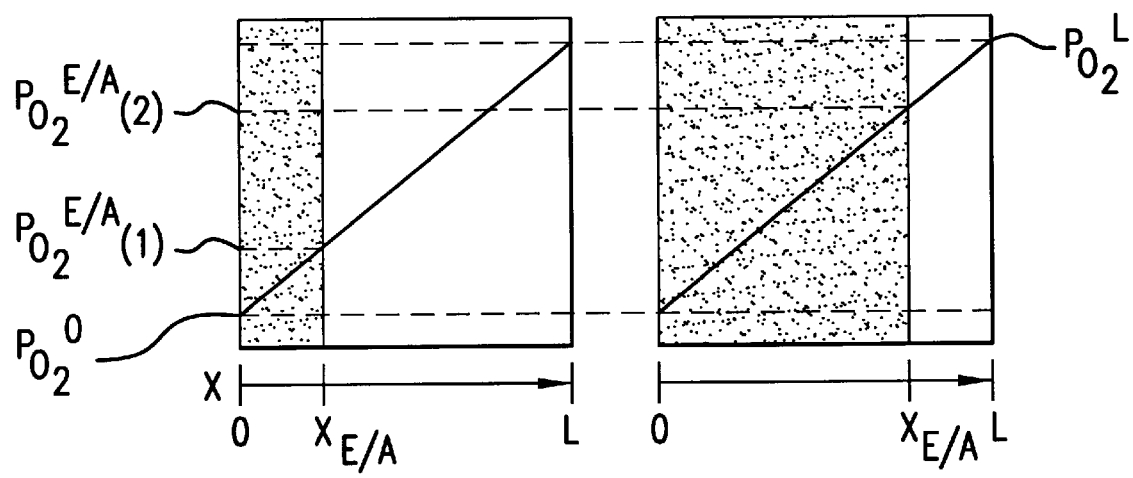
FIG. 1 are two graphs illustrating increase in local oxygen activity at the oxygen ion conducting electrolyte interface of a dense bi-layered electrolyte by increase in the thickness of mixed ionic-electronic conducting anode portion.

This invention utilizes the functional gradient across conductive layers to make advantageous use of superior conducting materials which individually would not be chemically stable in a desired use environment. By adjusting relative thicknesses of the layers of compositionally layered materials, an interface where the materials are stable may be achieved, due to the chemical gradient across the two layers. In this manner, an advantageous conductive pair of materials may be used as an electrolyte or membrane.

In a preferred embodiment, this invention provides a stable, high conductivity, functionally gradient, compositionally layered, solid membrane or electrolyte which comprises a dense ionic conducting layer capable of ionic conduction of an ion derived from a gas in contact with one face. The opposite face of the ionic conducting layer is in contact with one face of a mixed ionic-electronic conducting layer which has its opposite face in contact with and tolerant to an environment rendering the ion conducting layer chemically unstable. The mixed ionic-electronic conducting layer has sufficient thickness to raise the partial pressure of the gas from which the ions were derived to a sufficiently high level at the interface of the mixed ionic-electronic conducting layer and the ionic conducting layer to provide high chemical stability to the ionic conducting layer. In this manner, materials providing high ionic conduction at lower temperatures than previously used materials may be utilized in environments which have previously rendered these materials unsuitable. The ionic conducting layer is protected from the adverse gaseous environment in contact with the mixed ionic-electronic conducting layer by the thickness of the dense mixed ionic-electronic layer, tolerant to the adverse gaseous environment, providing at the interface of the mixed ionic-electronic conductor and the ionic conductor sufficiently high partial pressure of the gas from which the ions conducted by the ionic conducting layer were derived to assure chemical stability and ionic conductance of the ionic conducting layer.

It is apparent that many mixed ionic-electronic conductors and essentially exclusive ionic conductors may be matched to form functionally gradient and compositionally layered electrolytes according to this invention. Ions for conductance by the essentially exclusive ionic conductor may be derived from different gaseous sources, but oxygen ion conductance is described with reference to solid oxide fuel cells. Likewise, the essentially exclusive ionic conductor may be protected from different adverse gaseous environments by different mixed ionic-electronic conductors which are tolerant, or even, advantageously affected by such gaseous environments.

The invention will be described in greater detail and more specifically exemplified with respect to an electrolyte enabling long term stable operation of solid oxide fuel cells at temperatures of below about 800° C. An electrolyte comprising the combination of a dense bismuth oxide-based essentially exclusive oxygen ion conducting layer and a dense ceria-based mixed oxygen ion-electronic conducting layer has been found to be synergistic in providing high oxygen ion conductivity with minimal electronic conductivity, and thus high potential and power density, with the ceria-based mixed ionic-electronic conductor in contact with a reducing fuel environment. We have shown the stable operation of such electrolytes in the temperature range of about 500° to about 800° C. With thinner electrolyte assemblies than we used, it is reasonable to extrapolate that such electrolytes may be effective down to about 300° C. Therefore, suitable temperature ranges for operation of solid oxide fuel cells using the electrolytes of this invention are those less than about 800° C., preferably about 300° to about 800° C., and most preferably about 500° to about 800° C.

The ceria-based mixed ionic-electronic conducting layer is sufficiently thick to provide an oxygen partial pressure at the interface with the bismuth oxide-based essentially exclusive oxygen ion conducting layer of greater than about $10^{-20}$ and preferably greater than about $10^{-13}$ atm. In practice, this layer is less than about 1.0 mm and down to about 10 $\mu$m thick. The bismuth oxide-based oxygen ion conducting layer is suitably about 1 to about 30 $\mu$m thick. Thinner electrolytes are desirable because of their lower resistance.

The ceria is suitably doped with known dopants to enhance desired conductance. A number of dopants have been described above. We have found ceria doped with about 5 to about 20 mole percent of a lanthanide to be suitable, particularly suitable is samaria and gadolinia doped ceria.

The bismuth oxide is stabilized with known stabilizers to maintain high ionic conductance. A number of stabilizers have been described above. We have found bismuth oxide stabilized with about 10 to 30 mole percent of yttrium or a lanthanide, particularly suitable is yttrium and erbium stabilized bismuth oxide.

The bi-layered electrolyte having the formulation

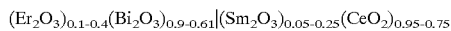

$(Er_2O_3)_{0.1-0.4}(Bi_2O_3)_{0.9-0.61}|(Sm_2O_3)_{0.05-0.25}(CeO_2)_{0.95-0.75}$ is particularly suitable for use as an electrolyte in a solid oxide fuel cell. The dense oxygen ion conducting layer maintains high essentially exclusive oxygen ion conduction at about 300° to about 800° C. when the mixed ionic-electronic conducting layer is sufficiently thick to raise the oxygen partial pressure at the interface of the two layers to greater than about $10^{-20}$, and preferably, greater than about $10^{-13}$ atm. A porous metal and/or metal oxide anode may be provided adjacent the open face of the mixed ionic-electronic conducting layer and a porous metal and/or metal oxide cathode provided adjacent the open face of the ionic conducting layer. Suitable current collectors and electrical leads, as known in the art, may be provided. Conventional means are provided for passing fuel gas in contact with the anode and for passing oxidant gas in contact with the cathode. In an alternative embodiment, electrical leads may be attached to the mixed ionic-electronic conducting layer and that layer of the electrolyte may function as an anode.

The bi-layered electrolyte based upon ceria and bismuth oxide may be fabricated at lower temperatures broadening the selection of cell components, reducing warpage, and making fabrication much easier. A thin layer of doped bismuth oxide is applied to an appreciably thicker pre-sintered ceria layer, prepared by any suitable process known to the art. We have found that the bismuth oxide layer may be applied by an aqueous slurry, but more desirable methods to obtain a thinner bismuth oxide layer may be sputter deposition, electrochemical vapor deposition, and various dip or spin coating methods. The bismuth oxide coated pre-sintered ceria layer is then sintered at temperatures of about 835° to about 1000° C., dependent upon the nature and amount of stabilizer used, to form the bi-layered electrolyte. Suitable sintering times are about 1 to about 10 hours, the longer times providing a denser bismuth oxide layer. In one embodiment, the bismuth oxide content of the ionic conducting layer may be enhanced by coating the sintered bi-layered electrolyte with pure bismuth oxide and then sintering at a temperature of about 835° to about 875°, the bismuth oxide serving as a low melting temperature flux to fill the pores in the ionic conducting layer for enhanced ionic conductivity.

The following Examples are set forth using specific materials and process conditions to illustrate this invention, and should not be considered to limit the invention in any manner.

EXAMPLE I

Yttrium and Samarium doped ceria electrolyte disks were prepared by tape casting and sintering. Powders of $M_2O_3$, where M=Y and Sm, and $CeO_2$ (99.99% purity, Cerac) were mixed in a $(M_2O_3)_{0.1}(CeO_2)_{0.9}$ ratio by wet ball milling with $ZrO_2$ balls and then calcined at 1300° C. The metal doped ceria powder was slurried in toluene and ball milled to reduce particle size. An organic binder (B-74001), dispersant (M-1201), and release agent (M-1111) from Palomar MSI were added to the slurry and mixed by ball milling. The slurries were cast onto a glass plate using an EPH tape caster with a doctor blade height of 2 mm. The cast tapes were dried at room temperature, removed from the glass plate, and cut into 3 cm diameter disks using a machined stainless steel punch. The green disks were placed into a Lindberg tube furnace with flowing $O_2$ and the temperature raised to 1000° C. at a temperature ramp of about 1° C./min to avoid warping and cracking. The disks were then cooled to room temperature and placed in a Thermolyne $MoSi_2$ furnace where they were sintered to 1650° C. for 15 hours. The disks were removed from the furnace and cooled to room temperature. The final sintered disks were 2.5 cm in diameter and about 0.8 mm thick.

One tape of yttria-doped ceria (YDC) and one tape of samaria-doped ceria (SDC) were prepared. The density of the sintered disks was determined with a Micromeritics He pycnometer and the percent of theoretical density for the YDC disks was 98.9% and the SDC disks was 91.0%. Higher density of the SDC disks would be desirable.

EXAMPLE II

Bi-layered electrolytes were prepared by first preparing doped ceria sintered disks, $(Y_2O_3)_{0.1}(CeO_2)_{0.9}$ and $(SM_2O_3)_{0.1}(CeO_2)_{0.9}$, as described in Example I. It is desirable to prepare these sintered disks first, since $CeO_2$ materials require sintering at greater than 1600° C. while $Bi_2O_3$ materials can be sintered at less than 900° C. Therefore, to fabricate the bi-layer electrolyte $M'_2O_3$-$Bi_2O_3|M_2O_3$-$CeO_2$ it is preferred to deposit and then sinter $M'_2O_3$-$Bi_2O_3$ onto presintered $M_2O_3$-$CeO_2$.

Pure $Bi_2O_3$ powder was ground in a mortar and pestle to 325 mesh (<40 $\mu$m), slurried in water and applied with a dropper to the surface of sintered disks of $(Sm_2O_3)_{0.1}(CeO_2)_{0.9}$ and $(Y_2O_3)_{0.1}(CeO_2)_{0.9}$ and sintered to 835° C. for 4 hours. The $Bi_2O_3$ melt-sintered, resulting in a dense thin film. The layered structure was confirmed by scanning electron micrographs. The migration of the dopant metal into the $Bi_2O_3$ layer by cation diffusion at the sintering temperature was confirmed with EDAX mapping of the cross section of the sintered bi-layered disks. Dense films of $Y_2O_3$-$Bi_2O_3$ and $Sm_2O_3$-$Bi_2O_3$ on YDC and SDC disks, respectively, were prepared by this simple method. However, the amount of dopant in the $M'_yO_3$-$Bi_2O_3$ layer was less than necessary for good conductivity and stabilization of the cubic phase which requires about 20 mol %.

EXAMPLE III

Fully stabilized $(Er_2O_3)_{0.2}(Bi_2O_3)_{0.8}$ (ESB) was deposited in the manner described in Example II on SDC disks prepared as described in Example I and sintered to 900° C. for one hour forming a bi-layered SDC|ESB electrolyte. The resulting film was continuous and adherent and its bi-layered structure confirmed by scanning electron micrographs. Two electrolytes were prepared and denoted as electrolytes SDC|ESB III-A and III-B.

EXAMPLE IV

Fully stabilized $(Er_2O_3)_{0.2}(Bi_2O_3)_{0.8}$ ESB was deposited on SDC disks, as described in Example III, except that the sintering temperature was 1000° C. for 4 hours forming a bi-layered SDCIESB electrolyte, denoted as SDC|ESB IV. The morphology of these bi-layered structures was more desirable due to the higher density of the ESB layer.

EXAMPLE V

Fully stabilized $(Er_2O_3)_{0.2}(Bi_2O_3)_{0.8}$ ESB was deposited on SDC disks, as described in Example III, except that the sintering temperature was 1000° C. for 10 hours following which the disks were cooled to room temperature. Pure $Bi_2O_3$ powder was ground, slurried and applied to the surface of the sintered disks which were then sintered at 850° C. for 6 hours. Thus, the SDC disks were first coated and sintered with ESB followed by coating and sintering the $Bi_2O_3$ which served as a low melting temperature flux to fill the porosity of the ESB layer forming a bi-layered SDC|ESB electrolyte, denoted as SDC|ESB V.

EXAMPLE VI

Laboratory cells were fabricated for solid oxide fuel cell evaluation of the electrolytes.

Porous Pt anodes and Au cathodes were used for these evaluations. Electrodes were deposited and sintered on each side of electrolyte disks to form metal|electrolyte|metal layered structures. Electrode deposition was achieved by brushing on a metal-suspension ink followed by drying and sintering. The geometric surface area of each electrode was 3.1 cm² in early cells and reduced to 1.0 cm² in later cells. The sintered electrodes had desired three dimensional porous morphology as determined by scanning electron microscopy, thickness of about 10 μm, and electrical resistance across the surface was measured to be typically 0.2 Ω.

The electrochemical cells were fabricated with the electrolyte disks having porous metal electrodes deposited on each side with attached external electrical leads, sealed gas-tight both to the external atmosphere and between opposite sides of the disk, all within a cell housing providing a fuel and oxidant chamber. The electrolyte cell was sealed using a low-melting-temperature glass, Corning 7059, seal around the circumference of the disk, which, upon heating, formed a positive pressure seal. The seals were confirmed by measuring inlet and outlet flows, with $O_2$ and $H_2$ flowing at 30 cm³/min on the cathode and anode, respectively, and for small diffusion leaks, open circuit potential was measured as function of temperature and time. Current-potential (I-E) data were obtained galvanostatically, potential as a function of applied current, for most of the cells, in the temperature range of 500° to 800° C.

EXAMPLE VII

Open circuit potentials $E_o$ for the cells was measured to demonstrate the higher value for $E_o$ obtained with bi-layered electrolytes according to this invention, approaching the theoretical $E_o$, while exhibiting stability against reduction of the electrolyte by $H_2$ at the anode. The theoretical $E_o$ for a solid oxide fuel cell at 800° C. with $H_2/3\%H_2O$ at the anode and pure $O_2$ at the cathode is:

$$E_o = \frac{RT}{zF}\ln\left(\frac{P^a_{O_2}}{P^b_{O_2}}\right) = \frac{(8.314)(1073)}{4(96,500)}\ln\left(\frac{1}{10^{-21}}\right) = 1.1V$$

where R is the gas constant (J/mol K), T is the temperature (K), z=equivalents/mol, F is the Faraday constant (Coulomb/equivalent), and $P^i_{O_2}$ is the oxygen partial pressure on side a and b of the cell. Due to thermodynamics of the $H_2/H_2O$ equilibria, $E_o$ increases slightly with decreasing temperature, 40 mV from 800° to 500° C. Theoretical $E_o$ can only occur with no electronic conduction across the electrolyte and no gas leak between the anode and cathode or to the external atmosphere.

Figure 2:
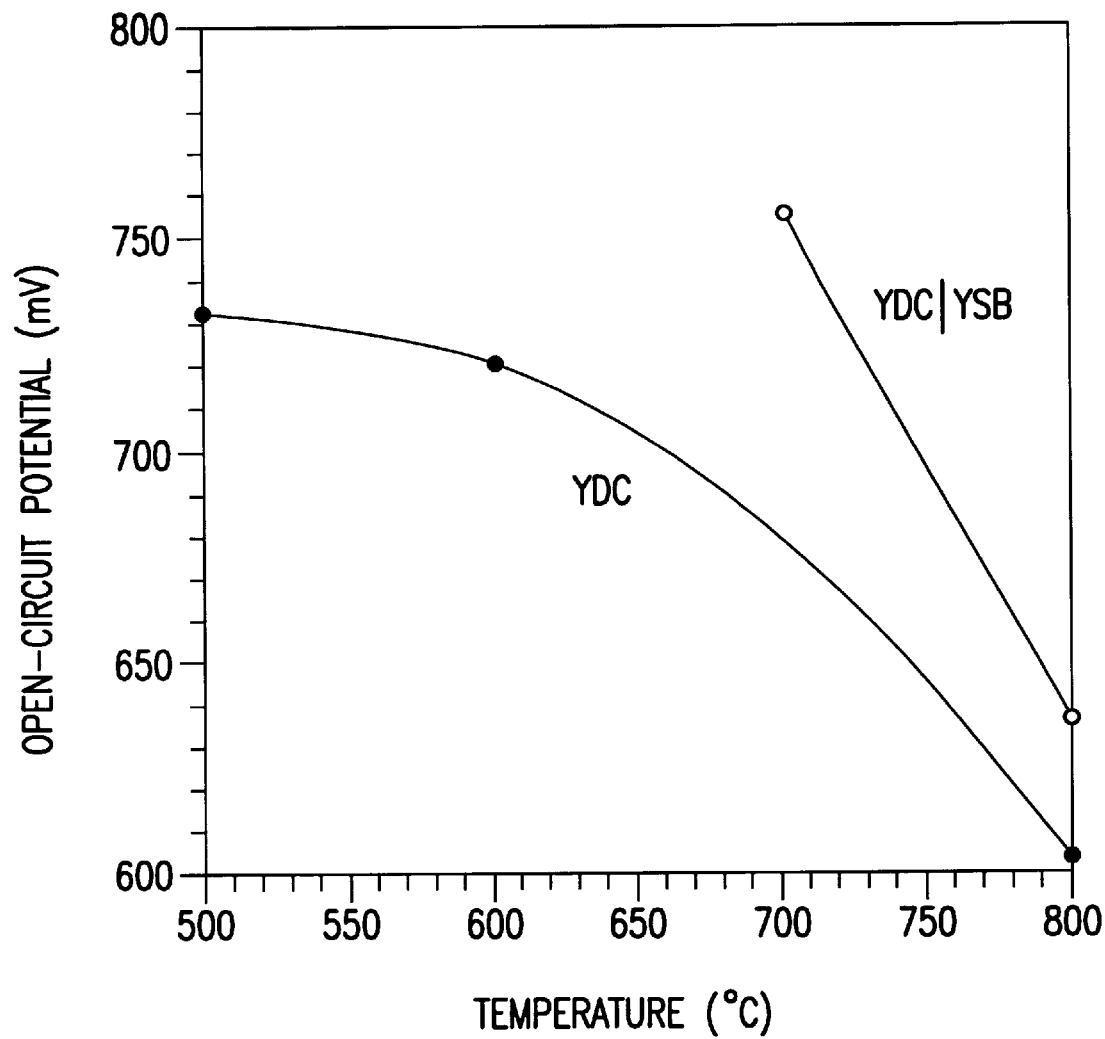
FIG. 2 compares plots of open circuit potential versus temperature for fuel cells having a mono-layered electrolyte and one having a bi-layered electrolyte as described in Example VII.

Cells were prepared in the manner described in Example VI using the YDC electrolyte as prepared in Example I, for comparison, and using the bi-layered YDC|YSB electrolyte as prepared in Example II according to this invention. The $E_o$ was measured at 500°, 600° and 800° C. for the YDC cell and at 700° and 800° C. for the YDC|YSB cell. The $E_o(T)$ data for these cells under identical conditions of $H_2/H_2O$-anode and $O_2$-cathode are shown in FIG. 2. It is seen than the YDC|YSB bi-layer electrolyte of this invention resulted in significantly higher $E_o$.

EXAMPLE VIII

Figure 3:
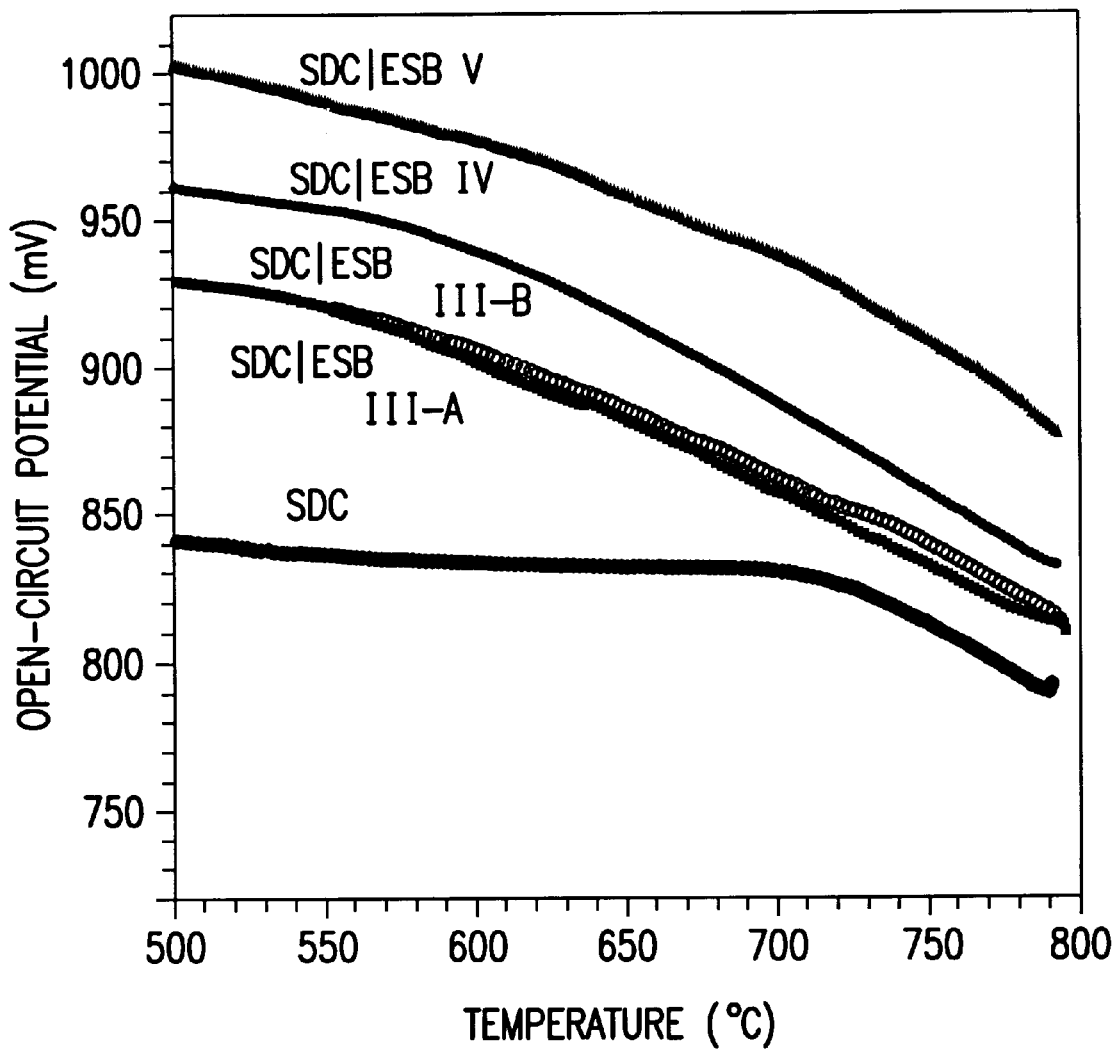
FIG. 3 compares plots of open circuit potential versus temperature for fuel cells having a mono-layered electrolyte and four having bi-layered electrolytes as described in Example VIII.

Five test cells were fabricated, as described in Example VI, based upon the Samarium-doped cerium electrolytes prepared in Examples I (SDC), III (SDC|ESB-III-A and III-B), IV (SDC|ESB-IV), and V (SDCIESB-V), and $E_o(T)$ data obtained from 500° to 800° C. in <1° increments under identical conditions of $H_2/H_2O$-anode and $O_2$-cathode are shown in FIG. 3. These results show than an $E_o$ of 840 mV was obtained with the SDC electrolyte cell at 500° C., compared with 730 mV for the YDC electrolyte cell, shown in FIG. 2, and that the $E_o$ of the SDC electrolyte cell is greater than that of the YDC electrolyte cell at all temperatures tested. This can be attributed to the higher $t_i$ of SDC as compared to YDC. The drop in $E_o$ with increasing temperature exhibited by the YDC and SDC electrolyte cells is primarily due to the $Ce^{+4}/Ce^{+3}$ equilibrium and resulting decrease in ionic domain of the ceria electrolytes with increasing temperature.

Also shown in FIG. 3 are the $E_o(T)$ measurements for cells using bi-layered SDC|ESB electrolytes:

III-A and III-B electrolytes as made in Example III;

IV electrolyte as made in Example IV; and

V electrolyte as made in Example V.

The bi-layered electrolytes according to this invention show significant increases in $E_o$ at all temperatures compared with the cell using the mono-layer SDC electrolyte. The increase in $E_o$ increased successively with electrolytes prepared in Examples III, IV, and V, due to improvement in the density of the ESB layer and resultant ability of the electrolyte to block electronic conduction. The cell fabricated from the bi-layered electrolyte prepared in Example V, obtained an $E_o$ of 1003 mV at 500° C. and overall a 90 to 160 mV increase in $E_o$, depending upon temperature, as compared to the mono-layer SDC electrolyte as prepared in Example I.

EXAMPLE IX

Test cells fabricated as described in Example VI were tested for current-potential data using porous metal electrodes, except SDC|ESB-V which had a $LaSrCoO_3$ cathode and Ni-Ceria anode, with O$_2$-cathode and H$_2$-anode at 800° C. The results are summarized in Table 1.

The cell resistance was determined by a linear fit (slope) of the I-E data and is shown in Table 1. The cell resistance, normalized on a geometric electrode surface area, showed a decrease for the cells using a bi-layered electrolyte of this invention. The actual I-E data had a slight positive curvature, typical of mixed conductors, and dominated by non-electrolyte, e.g. electrode, polarization. The resistance of the 0.8 mm thick SDC electrolyte was only 0.88 Ωcm$^2$ at 800° C. Electrolyte performance may still be compared, based upon cell performance, since the cells were identically fabricated. The lower resistance of the SDC cell relative to the YDC cell is attributed to its higher conductivity. Most importantly, is that the bi-layered electrolyte fabrication according to this invention did not increase the cell resistance, but in fact decreased cell resistance by 23±7%, for the SDC cells.

TABLE 1

Cell Performance

| Electrolyte | E$_0$ (mV) | Cell Resistance (Ω cm$^2$) | Maximum Power Density (mW/cm$^2$) |
|---|---|---|---|
| YDC | 605 | 4.8 | 18 |
| YDC\|YSB | 640 | * | * |
| SDC | 790 | 3.8 | 40 |
| SDC\|ESB III-A | 810 | 2.7 | 53 |
| SDC\|ESB III-B | 820 | 3.2 | 47 |
| SDC\|ESB IV | 835 | 2.9 | 51 |
| SDC\|ESB V | 880 | * | * |

*Measurements could not be made due to high contact resistance.

Figure 4:
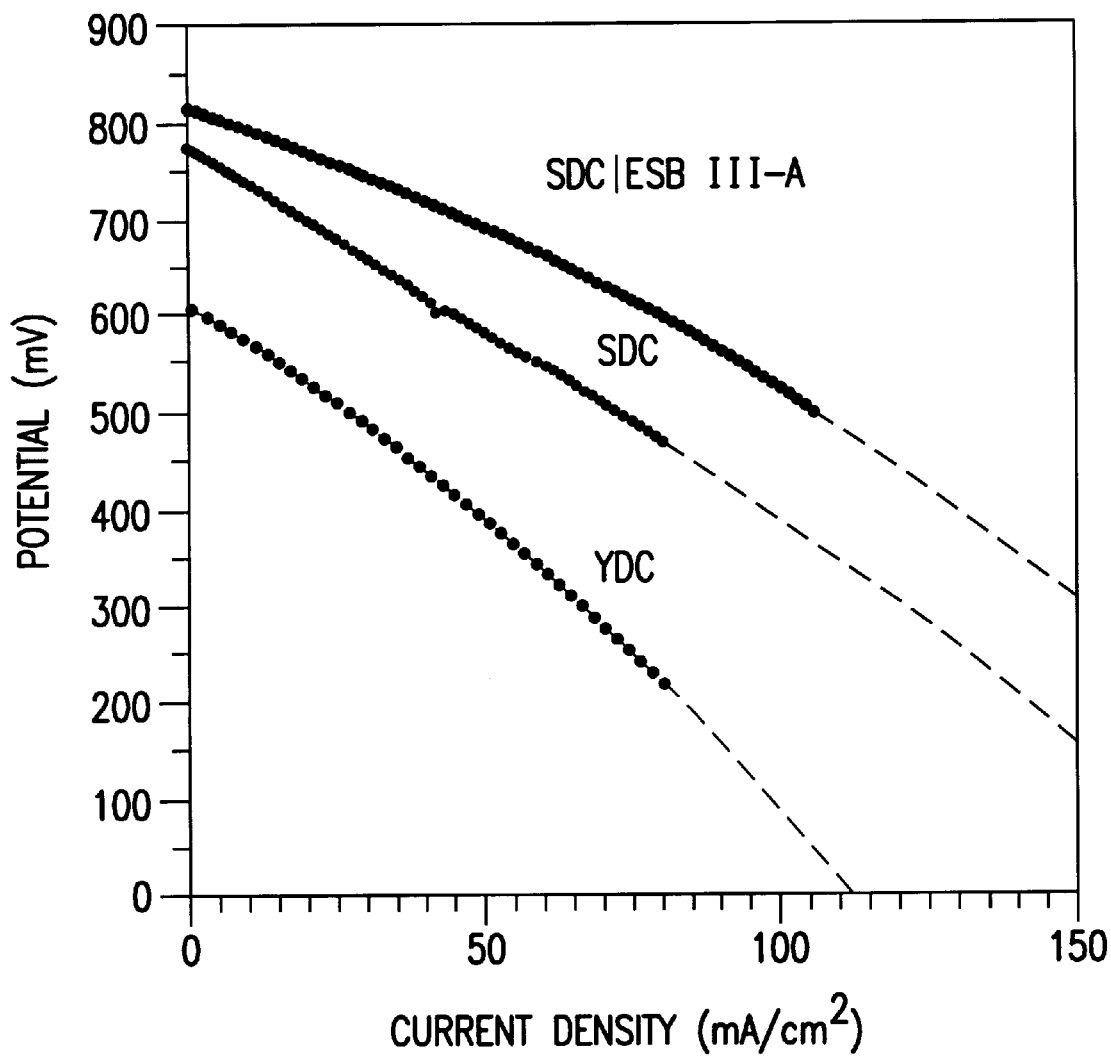
FIG. 4 compares plots of potential versus current density for two fuel cells having mono-layered electrolytes and one having a bi-layered electrolyte as described in Example IX.

The potential is plotted as a function of current density for cells YDC, SDC, and SDC|ESB III-A at 800° C. in FIG. 4. The current density was calculated from the current and the geometric surface area of the electrodes. The data were curve fit and extrapolated to higher current densities shown by the dashed lines.

Figure 5:
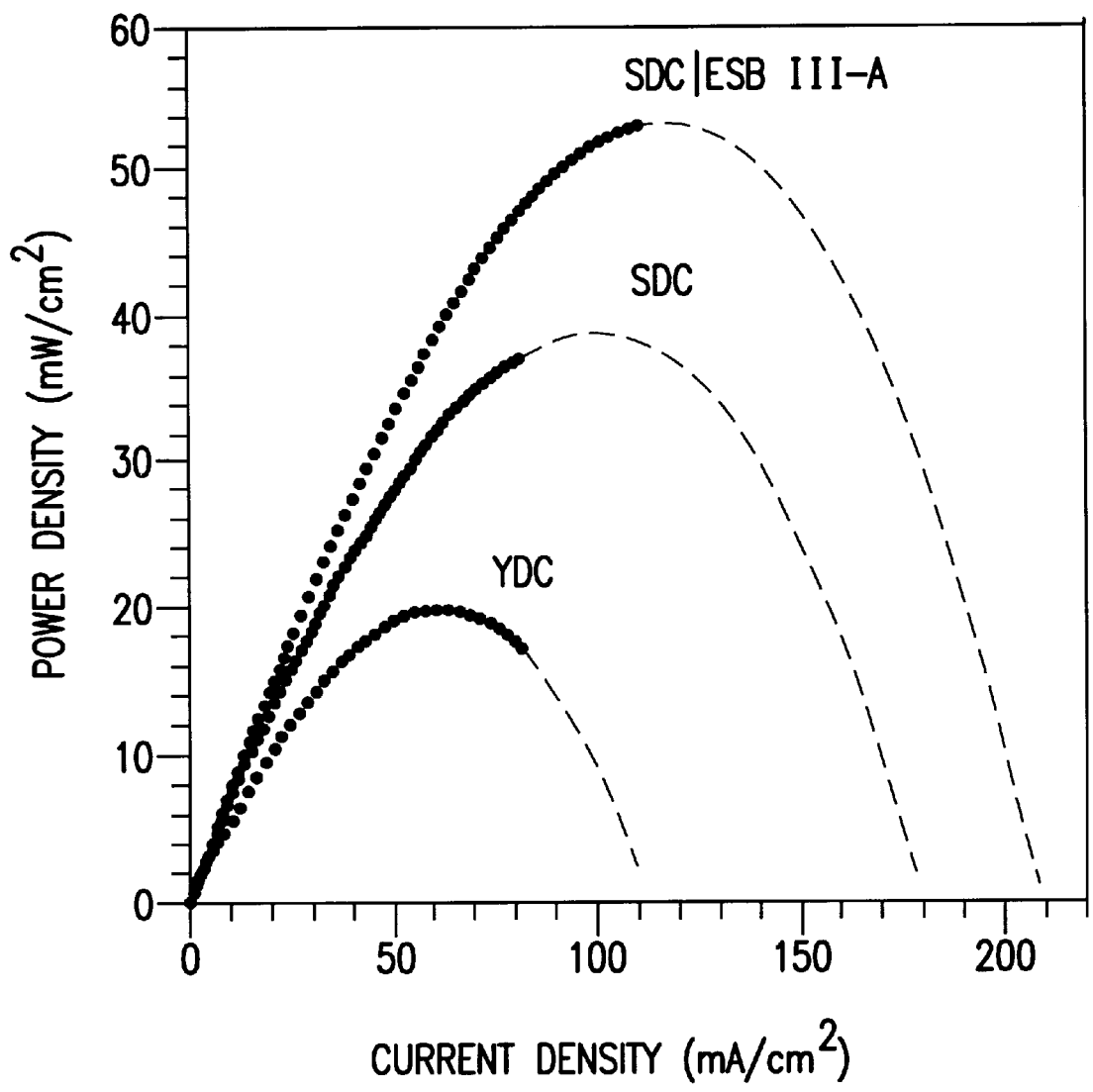
FIG. 5 compares plots of power density versus current density for the same fuel cells for which data is shown in FIG. 4 and described in Example IX.

The I-E data were replotted in terms of power density for cells YDC, SDC, and SDC|ESB III-A at 800° C. in FIG. 5 showing the power density for the bi-layered SDC|ESB III-A electrolyte of this invention to be 33% greater than the SDC mono-layer electrolyte under identical conditions. The data were curve fit and extrapolated to higher current densities shown by the dashed lines.

Figure 6:
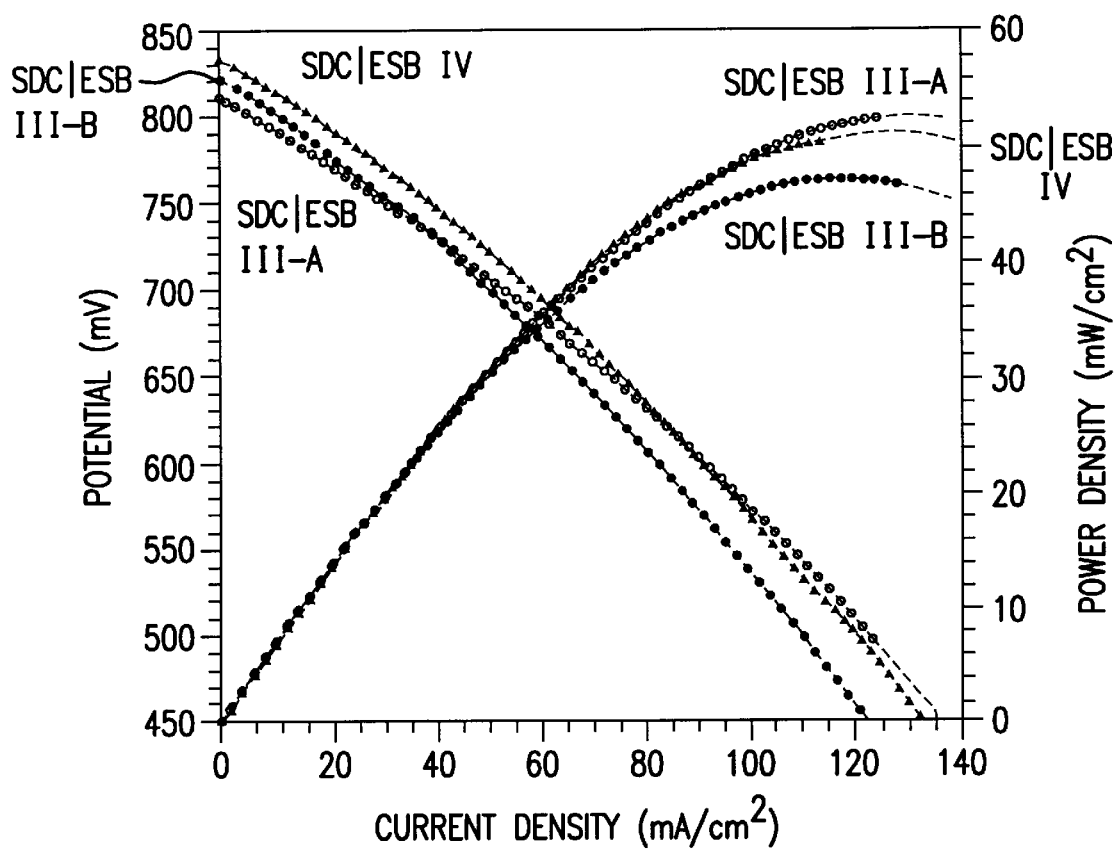
FIG. 6 shows reproducibility of plots of potential and power density versus current density for fuel cells having bi-layered electrolytes as described in Example IX.

The reproducibility of the current-potential behavior of the cells incorporating bi-layered electrolytes according to this invention is shown in FIG. 6. The increase in E$_o$ from SDC|ESB III-A and III-B to SDC|ESB IV is as expected, due to the electrolyte improvement. The variation in cell resistance, and hence power density, is relatively small and most likely due to variation in electrode response, which was not either optimized or fully characterized.

Figure 7:
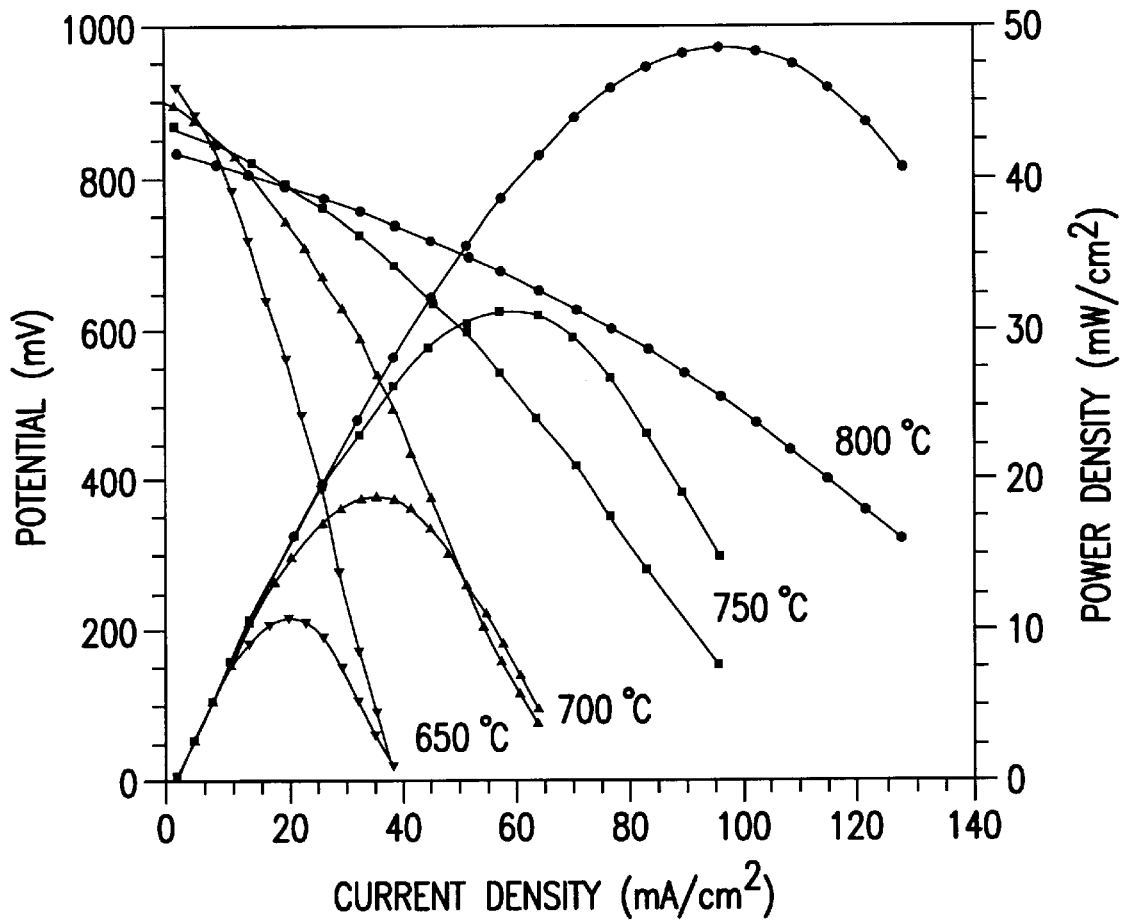
FIG. 7. shows plots of potential and power density versus current density at temperatures of 650° to 800° C. for a fuel cell having a bi-layered electrolyte as described in Example IX.

The typical temperature dependence of the current-potential behavior and power density of the cells fabricated using bi-layered electrolytes according to this invention is shown in FIG. 7 using a SDC|ESB IV electrolyte 0.8 mm thick, as prepared in Example IV, using simple porous metal electrodes.

EXAMPLE X

Figure 8:
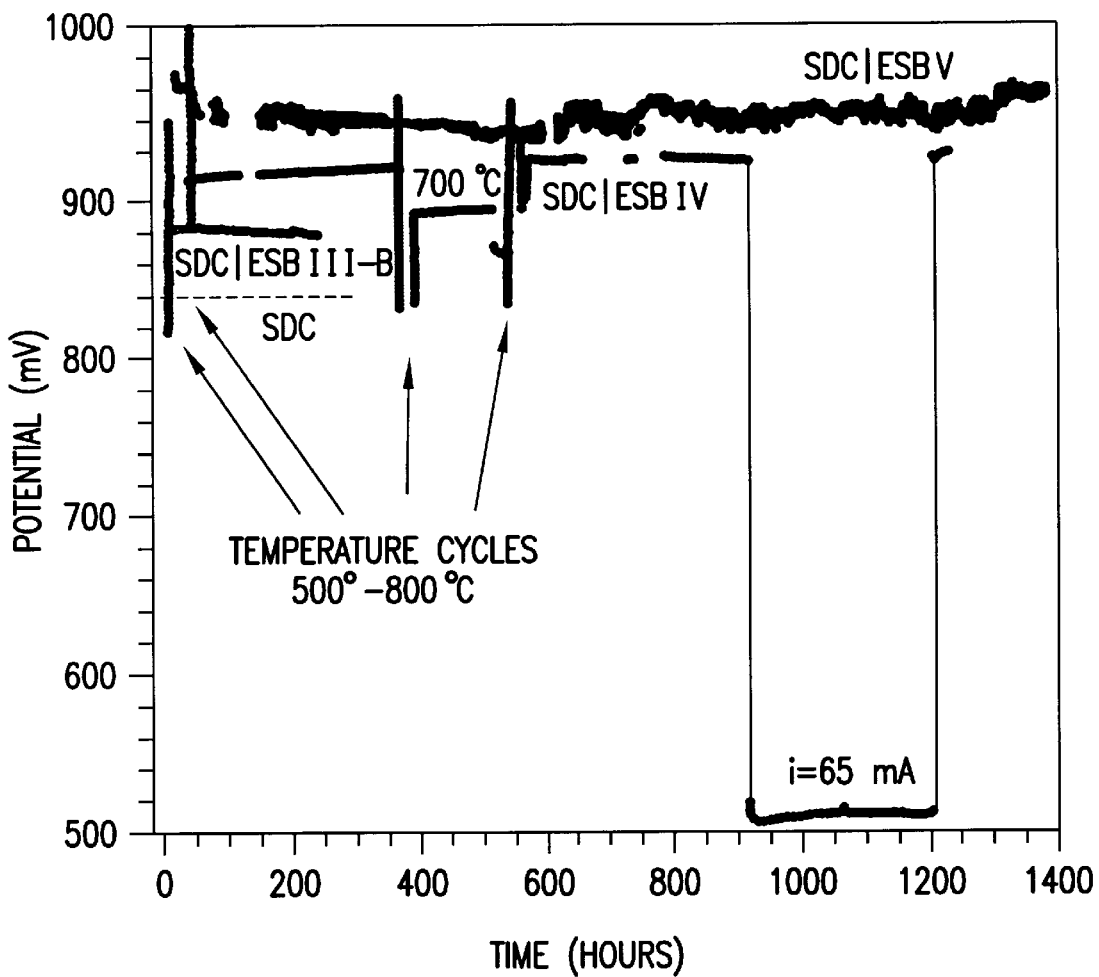
FIG. 8 shows plots of potential versus time showing stability of fuel cells having bi-layered electrolytes as described in Example X.

All SDC-based cells prepared in Examples I, III, IV, and V were thermally cycled several time for electrode deposition and sealing and were found to operate well without any sign of mechanical failure. The stability of the bi-layered electrolytes of this invention under open circuit and maximum power conditions is shown in FIG. 8. A dashed line at 840 mV indicates the E$_o$ of the cell using the single layered SDC electrolyte for comparison under identical conditions of gas composition and temperature.

The cell using the SDC|ESB III-B electrolyte was operated for one day at various temperatures for I-E and E$_o$ data and then run continuously for an additional 250 hours at 650° C. under open circuit conditions with no decrease in E$_o$, as shown in FIG. 8. Over this time period the E$_o$ was quite constant at 882±1 mV. The current-potential curves before and after the stability test were essentially superimposable, further demonstrating the stability of the cell.

The cell using the SDC|ESB IV electrolyte was operated continuously for 1250 hours. For the first 900 hours, the cell was primarily under open circuit conditions at 650° C., except where noted for thermal cycling and I-E data acquisition. After the first 900 hours, the cell was operated at maximum power conditions of 65 mA for 300 hours and then returned to open circuit for 10 hours, at which time a crack developed due to water buildup at the anode. Over the entire time period, the cell readings were relatively noise-free and demonstrated a continuous increase in potential under both open circuit and maximum power conditions. At the beginning of the test, E$_o$ was 910 mV, and after 1250 hours of operation, it had increased to 935 mV. The I-E data also demonstrated a continuous increase in power density with time.

The cell using the SDC|ESB V electrolyte was operated continuously for 1400 hours until a power outage caused shut down of the cell. The cell had a continuously high E$_o$ which appeared to increase near the end of the test. The scatter of the data was due to a contact problem associated with the LaSrCoO$_3$ cathode and Ni-ceria anode. To confirm that the E$_o$ was correct, the H$_2$ was temporarily shut off during the test and E$_o$ dropped and recovered, as expected.

Based upon the results described above, it is reasonable to project that improved electrolyte density would result in a significant increase in open circuit potential, approaching theoretical. With improvements such as thinner electrolytes and better electrodes, increased power density on the order of 1000 mW/cm$^2$, at low operating temperatures of below 800° C., are achievable.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

We claim:

1. A stable high conductivity compositionally layered solid body comprising: a dense functionally gradient first conducting layer having a first function which is chemically stable in the environment of a first gas, said first conducting layer in contact with a dense functionally gradient second conducting layer having a second function which is chemically stable in the environment of a second gas which renders said first conducting layer chemically unstable, said functional gradients being due to a chemical gradient across each of said first conducting layer and said second conducting layer, said first conducting layer and said second conducting layer having relative thicknesses to achieve an interface at which chemical stability of each layer may be achieved, due to the chemical gradients across the layers.

2. A layered solid body according to claim 1 wherein said first gas to which said first conducting layer is chemically stable is oxygen and said second gas which renders said first conducting layer chemically unstable is a reducing gas.

3. A layered solid body according to claim 2 wherein said solid body is a membrane having transport number $t_i$ less than about 0.95 and having high electronic conduction throughout.

4. A layered solid body according to claim 3 having conductive regions selected from the group consisting of p-type, n-type and n-type|p-type having no intrinsic region providing electronic conduction throughout.

5. A layered solid body according to claim 3 wherein said layers are mixed oxygen ion-electronic conducting layers having relative thicknesses sufficient to provide an oxygen partial pressure at the interface of said layers to maintain said chemical stability of each said layer when one of said layers is in contact with an oxidizing environment and the other said layer is in contact with a reducing environment.

6. A layered solid body according to claim 5 wherein one of said mixed oxygen ion-electronic conducting layers comprises ceria based material.

7. A layered solid body according to claim 6 wherein said mixed oxygen ion-electronic conducting layer has the chemical formulation $MO_x\text{-}CeO_2$ wherein M is a single metal or mixture of metals selected from the group consisting of Ca, Sr, Ba, Y, Zr, Nb, Mo, Hf, W, La, Pr, Nd, Pm, Sm, Eu, Gd, Tb, Dy, Ho, Er, Tm, Yb, and Lu.

8. A layered solid body according to claim 5 wherein one of said mixed oxygen ion-electronic conducting layers comprises mixed metal oxide.

9. A layered solid body according to claim 8 wherein one of said mixed oxygen ion-electronic conducting layers comprises bismuth oxide based material.

10. A layered solid body according to claim 9 wherein said mixed oxygen ion-electronic conducting layer has the chemical formulation $Bi_{2-x-y}M'_xM_yO_{3-\delta}$ wherein M' is selected from the group consisting of Er, Y, Tm, Yb, Tb, Lu, Nb, Sm, Dy, Zr, Hf, Th, Ta, Nb, Pb, Sn, In, Ca, Sr, La and mixtures thereof; M is a variable valence metal selected from the group consisting of Mn, Fe, Ni, Cu and mixtures thereof; x is a number of 0.0 to a positive number of about 0.6; y is a positive number of about 0.02 to about 0.4; and $\delta$ is of to satisfy valence requirements.

11. A layered solid body according to claim 8 wherein one of said mixed oxygen ion-electronic conducting layers comprises a perovskite type structure material.

12. A layered solid body according to claim 11 wherein said perovskite type structure material has the chemical formulation $ABO_3$ wherein A is a metal selected from the group consisting of lanthanides, yttrium, alkaline earth metals and mixtures thereof and B is selected from the group of transition metals and mixtures thereof.

13. A layered solid body according to claim 12 wherein said perovskite type material contains two to five metals.

14. A layered solid body according to claim 12 wherein said perovskite type material is selected from the group of mixed metal oxides consisting of lanthanum-strontium manganite, lanthanum-strontium cobaltite, lanthanum-strontium-iron chromite, lanthanum-strontium-iron-chromium cobaltite, lanthanum-strontium-iron-chromium manganite, lanthanum-calcium-iron chromite, lanthanum-calcium-chromium cobaltite, lanthanum-calcium-iron-chromium manganite, lanthanum-magnesium chromite, lanthanum-chromium ferrite, lanthanum cobaltite, yttrium-strontium-iron chromite, yttrium-strontium-iron-chromium cobaltite, yttrium-strontium-iron-chromium manganite and yttrium-barium cuprite.

15. A stable high conductivity functionally gradient compositionally layered membrane, comprising; a first dense mixed oxygen ion-electronic conducting layer having oxygen ion and electronic conduction at about 500° to about 800° C. and having a first face stable in an oxidizing atmosphere and an opposite second face in contact with one face of a second dense mixed oxygen ion-electronic conducting layer having oxygen ion and electronic conduction at said temperature, said second layer having its opposite face resistant to decomposition by a reducing environment which renders said first layer unstable, said first and second mixed oxygen ion-electronic conducting layers having sufficient relative thicknesses to maintain an oxygen partial pressure at the interface of said layers to provide high chemical stability of each said oxygen ion-electronic conducting layers.

16. A stable high conductivity functionally gradient compositionally layered membrane according to claim 15 having conductive regions selected from the group consisting of p-type, n-type and n-type|p-type having no intrinsic region providing electronic conduction throughout.

17. A stable high conductivity functionally gradient compositionally layered membrane according to claim 15 wherein one of said mixed oxygen ion-electronic conducting layers comprises ceria based material.

18. A stable high conductivity functionally gradient compositionally layered membrane according to claim 17 wherein said mixed oxygen ion-electronic conducting layer has the chemical formulation $MO_x\text{-}CeO_2$ wherein M is a single metal or mixture of metals selected from the group consisting of Ca, Sr, Ba, Y, Zr, Nb, Mo, Hf, W, La, Pr, Nd, Pm, Sm, Eu, Gd, Tb, Dy, Ho, Er, Tm, Yb, and Lu.

19. A stable high conductivity functionally gradient compositionally layered membrane according to claim 15 wherein one of said mixed oxygen ion-electronic conducting layers comprises mixed metal oxide.

20. A stable high conductivity functionally gradient compositionally layered membrane according to claim 19 wherein one of said mixed oxygen ion-electronic conducting layers comprises bismuth oxide based material.

21. A stable high conductivity functionally gradient compositionally layered membrane according to claim 20 wherein said mixed oxygen ion-electronic conducting layer has the chemical formulation $Bi_{2-x-y}M'_xM_yO_{3-\delta}$ wherein M' is selected from the group consisting of Er, Y, Tm, Yb, Tb, Lu, Nb, Sm, Dy, Zr, Hf, Th, Ta, Nb, Pb, Sn, In, Ca, Sr, La and mixtures thereof; M is a variable valence metal selected from the group consisting of Mn, Fe, Ni, Cu and mixtures thereof; x is a number of 0.0 to a positive number of about 0.6; y is a positive number of about 0.02 to about 0.4; and $\delta$ is of to satisfy valence requirements.

22. A stable high conductivity functionally gradient compositionally layered membrane according to claim 15 wherein one of said mixed oxygen ion-electronic conducting layers comprises a perovskite type structure material.

23. A stable high conductivity functionally gradient compositionally layered membrane according to claim 22 wherein said perovskite type structure material has the chemical formulation $ABO_3$ wherein A is a metal selected from the group consisting of lanthanides, yttrium, alkaline earth metals and mixtures thereof and B is selected from the group of transition metals and mixtures thereof.

24. A stable high conductivity functionally gradient compositionally layered membrane according to claim 23 wherein said perovskite type material contains two to five metals.

25. A stable high conductivity functionally gradient compositionally layered membrane according to claim 24 wherein said perovskite type material is selected from the group of mixed metal oxides consisting of lanthanum-strontium manganite, lanthanum-strontium cobaltite, lanthanum-strontium-iron chromite, lanthanum-strontium-iron-chromium cobaltite, lanthanum-strontium-iron-chromium manganite, lanthanum-calcium-iron chromite, lanthanum-calcium-chromium cobaltite, lanthanum-calcium-iron-chromium manganite, lanthanum-magnesium chromite, lanthanum-chromium ferrite, lanthanum cobaltite, yttrium-strontium-iron chromite, yttrium-strontium-iron-chromium cobaltite, yttrium-strontium-iron-chromium manganite and yttrium-barium cuprite.

* * * * *